(12) United States Patent
Nagarkatti et al.

(10) Patent No.: US 8,242,178 B2
(45) Date of Patent: Aug. 14, 2012

(54) USE OF CANNABIDIOL IN THE TREATMENT OF AUTOIMMUNE HEPATITIS

(75) Inventors: Prakash S. Nagarkatti, Columbia, SC (US); Mitzi Nagarkatti, Columbia, SC (US)

(73) Assignee: University of South Carolina, Columbia, SC (US)

( * ) Notice: Subject to any disclaimer, the term of this patent is extended or adjusted under 35 U.S.C. 154(b) by 606 days.

(21) Appl. No.: 12/141,634

(22) Filed: Jun. 18, 2008

(65) Prior Publication Data

US 2009/0005461 A1    Jan. 1, 2009

Related U.S. Application Data

(60) Provisional application No. 60/936,040, filed on Jun. 18, 2007.

(51) Int. Cl.
*A61K 31/47*    (2006.01)

(52) U.S. Cl. ...................................................... 514/733
(58) Field of Classification Search .................. None
See application file for complete search history.

(56) References Cited

U.S. PATENT DOCUMENTS 7,105,685 B2 * 9/2006 Travis .......................... 549/390
2006/0039959 A1 * 2/2006 Wessling ..................... 424/448

OTHER PUBLICATIONS

Czaja, A.J., Digestive Disease Sci., 55(6), (Jun. 2010), pp. 1761-1769 (abstract).*
Vella et al., Recenti Prog. Med., (Oct. 2004), 95(10); 472-5 (Abstract).*

* cited by examiner

*Primary Examiner* — Phyllis G. Spivack
(74) *Attorney, Agent, or Firm* — Dority & Manning, P.A.

(57) ABSTRACT

Methods of treating autoimmune hepatitis are provided. The methods include injecting cannabidiol into the subject, where the cannabidiol is synthetic cannabidiol or natural cannabidiol isolated from other natural cannabinoids.

6 Claims, 11 Drawing Sheets

USE OF CANNABIDIOL IN THE TREATMENT OF AUTOIMMUNE HEPATITIS

PRIORITY INFORMATION

The present application claims priority to U.S. Provisional Patent Application Ser. No. 60/936,040 filed on Jun. 18, 2007, entitled "Use of Cannabinoids in the Treatment of Hepatitis", which is incorporated by reference herein.

GOVERNMENT SUPPORT CLAUSE

The present invention was developed with funding from the National Institutes of Health grant 5R01DA016545-05. The government retains certain rights in this invention.

BACKGROUND

Liver disease is a major cause of morbidity and mortality and the prognosis is often poor. In many liver diseases (such as viral hepatitis, autoimmune hepatitis and alcoholic liver disease), activated T lymphocytes and macrophages appear to play an important role in liver damage. Autoimmune hepatitis is an inflammatory liver disease characterized by the presence of high transaminases, circulating autoantibodies, hypergammaglobulinemia, histological evidence of hepatitis and responsiveness to immunosuppressive treatment. In autoimmune hepatitis, activated T cells and macrophages either directly attack liver parenchymal cells or induce tissue damage by the release of several proinflammatory cytokines, such as TNF-$\alpha$ and IFN-$\gamma$.

The precise cause of autoimmune hepatitis is not clear. Environmental agents assumed to induce autoimmune hepatitis have not been delineated but include viruses and bacteria. The finding of molecular mimicry by cross-reactivity between epitopes of viruses and certain liver antigens adds credence to a hypothesis of virally triggered disease. Because the trigger or triggers of autoimmune hepatitis may be part of a so-called hit-and-run phenomenon, in which induction occurs many years before overt autoimmune disease, identifying an infectious agent may prove impossible. However, evidence does exist implicating measles virus, hepatitis viruses, cytomegalovirus, and Epstein-Barr virus as initiators of the disease; with the most convincing evidence related to hepatitis viruses. Autoimmune hepatitis is more common among women than men, but it occurs globally in children and adults of both sexes in diverse ethnic groups. Since chronic viral hepatitis appears to be very common, the prevalence of autoimmune hepatitis may be higher than reported because of concomitant chronic hepatitis C or B or both. Certain drugs, including oxyphenisatin, methyldopa, nitrofurantoin, diclofenac, interferon, pemoline, minocycline, and atorvastatin, can induce hepatocellular injury that mimics autoimmune hepatitis.

There are three experimental mouse models of T cell dependent liver injury. D-galactosamine (GalN)-sensitized mice challenged with either T cell activating anti-CD3 monoclonal antibody (mAb) or with the superantigen staphylococcal enterotoxin B (SEB) developed severe liver injury characterized by internucleosomal DNA fragmentation as well as by histological hallmarks of hepatocyte apoptosis, both preceding the increase of plasma transaminases. Administration of the T cell mitogen concanavalin A (Con A) to unsensitized mice also resulted in hepatic apoptosis and the ensuing necrosis. Anti-CD3 mAb as well as SEB or Con A induced the release of systemic tumor necrosis factor (TNF), interferon gamma (IFN-$\gamma$), and various other cytokines. T lymphocytes were identified as effector cells of Con A in vivo by proof of resistance of athymic nude mice against Con A and by restoration of susceptibility in nude mice by lymphocyte transfer from control mice. Moreover, antibody-dependent depletion of CD4+ T cells fully protected against Con A. These results indicated that cytokines released following T helper cell activation mediated liver injury. Con A-induced liver damage mimics human viral and autoimmune hepatitis in many aspects. These include an increase in the serum concentration of several cytokines including TNF-$\alpha$, IFN-$\gamma$, IL-6, and IL-1. During the early stages, TNF-$\alpha$ and IFN-$\gamma$ directly mediate liver cell damage. The cell types involved in the induction of Con A-induced hepatitis include neutrophils, CD4$^+$ T cells, CD8$^+$ T cells, $\alpha\beta$T, NK T cells and Kupfer cells which have been directly implicated in autoimmune, viral, alcoholic hepatitis, and ischemia/reperfusion injury.

Autoimmune hepatitis in humans is classified as either type I or II, based on the presence of anti-nuclear (ANA) and/or smooth muscle (SMA) antibodies in type I, and liver/kidney microsomal antibody for type II. The ten-year survival rate in untreated patients is approximately 10%. Both types of autoimmune hepatitis are treated with corticosteroids such as prednisone as well as other immunosuppressive drugs such as azathioprine, mycophenylate mofetil, cyclosporine or tacrolimus. Patients who progress to end stage liver disease and/or cirrhosis may also need a liver transplant. Therefore, alternative treatment options are needed. Therapeutic approaches that either inhibit immune-mediated mechanisms or directly inhibit liver cell damage show promise. These studies have addressed the mechanism underlying use of CAM therapy in ameliorating hepatitis and liver damage. While extensive studies have been performed to elucidate the mechanism of viral hepatitis, there is paucity of information on the pathogenesis of autoimmune hepatitis and a dire need for the development of CAM therapy to treat such patients.

Complementary and alternative medicine (CAM) is popular amongst patients with hepatitis. A recent survey conducted in liver disease outpatient clinics in the US found that 41% had used some form of CAM at least once during the preceding 4 weeks. The CAM therapies tried out clinically include antioxidants, thymic extract, zinc, Chinese herbs, *Glycyrrhiza glabra* (licorice), and Oxymatrine (derived from *Sophora japonica*). Several herbal medicinal products and supplements have been identified with potential virological and/or biochemical effects in the treatment of chronic hepatitis C infection. Studies of thymic extract, zinc and Bing Gan decoction in combination with interferon-☐ and oxymatrine alone have demonstrated greater clearance of the hepatitis C virus than control treatment. Normalization of liver enzymes has been greater during treatment with vitamin E, *Glycyrrhiza glabra*, CH100, Yi Zhu decoction and Yi Er Gan Tang decoction than with the control treatment. Evidence suggests that many more complementary therapies are currently available to and popular with patients and further research into these interventions is warranted to establish their role in the treatment of hepatitis.

SUMMARY

The present disclosure introduces CB2 selective agonists, devoid of psychotropic effect, that can trigger apoptosis in immune cells and act as novel anti-inflammatory/immunosuppressive agents, for instance in treating hepatitis.

For example, in one embodiment, disclosed is a method of treating hepatitis in a subject, the method including identifying a subject suffering from or at risk for hepatitis. The method further comprising administering cannabidiol to the subject. More specifically, the cannabidiol can be synthetic cannabidiol or natural cannabidiol isolated from other natural cannabinoids.

According to another embodiment, disclosed is a method for inducing apoptosis of thymocytes in a subject, the method comprising administering to a subject an amount of cannabidiol greater than about 100 milligrams cannabidiol per kilogram mass of the subject, wherein upon administration of the cannabidiol, thymic cellularity of the subject decreases.

According to another embodiment, disclosed is a method for inducing apoptosis of splenocytes in a subject, the method comprising administering to a subject an amount of cannabidiol greater than about 50 milligrams cannabidiol per kilogram mass of the subject, wherein upon administration of said cannabidiol, splenic cellularity of said subject decreases.

In yet another embodiment, disclosed is a method for decreasing the level of plasma aspartate transaminase in a subject, the method comprising administering cannabidiol to a subject exhibiting elevated levels of plasma aspartate transaminase, wherein following administration of the cannabidiol, the subject's level of plasma aspartate transaminase decreases.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which:

FIG. 14 shows the effect of CBD on Con A-induced autoimmune hepatitis. C57BL/6 mice were injected with PBS (control), or ConA (12.5 mg/kg bodyweight, i.v.) to induce hepatitis. ConA injected mice were administered (i.p.) with ethanol vehicle (ConA+Veh group) or CBD, 50 mg/kg bodyweight (ConA+CBD group). CBD group received CBD alone. In the left panel, blood was collected at 6, 12, 24, and 48 hours by retro-orbital bleeding. Plasma AST (aspartate transaminase) was determined by spectrophotometry using AST assay kit. The decrease in AST values for ConA+CBD group compared to ConA+Veh group was analyzed by Student's t test (*p<0.05, **p<0.01). Right panel shows photomicrographs of representative livers obtained 48 hours post ConA injection with H&E staining (original magnification ×100). A, PBS; b, ConA+Veh; c, ConA_CBD; d, CBD alone.

DETAILED DESCRIPTION

Reference now will be made in detail to embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

Generally speaking, the present disclosure is directed to methods for triggering apoptosis in immune cells and act as anti-inflammatory/immunosuppressive agents for treating hepatitis through the administration of cannabidiol ("CBD"). In particular, the present disclosure identifies apoptotic mechanisms induced by cannabidiol in immune cells.

Specifically, the present disclosure is directed to the following findings:
1. CBD can induce apoptosis in thymocytes and splenocytes in vitro, and when injected in vivo, can cause decreased cellularity in the thymus and spleen, thereby showing that CBD can act on naïve cells.
2. CBD can inhibit the proliferative responsiveness of T and B cells independently of CB1 and CB2 receptors.
3. CBD-induced apoptosis can be caspase-dependent, involving both the intrinsic and extrinsic pathways.
4. CBD-mediated apoptosis in normal T cells is regulated primarily through vanilloid receptors and to a minor degree with CB2. In contrast, CBD-induced apoptosis in transformed T cells is primarily mediated through CB2.
5. CBD suppresses the staphylococcal enterotoxin B (SEB)-induced activation of Vβ8+ T cells in vivo.
6. Cannabinoids, such as THC, downregulate the Raf/MEK/ERK/RSK pathway in Jurkat T cells thereby facilitating translocation of Bad to the mitochondria and consequent apoptosis.
7. CBD effectively protects the host from autoimmune hepatitis induced by ConA as evidenced by decreased AST levels and marked decrease in inflammatory response.

Cannabidiol

CBD is non-psychoactive and can trigger apoptosis in immune cells as well as act as an anti-inflammatory agent. This opens new avenues with wide-ranging clinical application in the treatment of autoimmune hepatitis as well as other inflammatory disease. The chemical structure of cannabidiol can be represented as follows:

CBD is a compound belonging to a broader class of cannabinoids. Cannabinoids are a heteromorphic group of chemicals which activate the body's cannabinoid receptors. Initially cannabinoids were discovered in *Cannabis sativa*, the cannabis plant. There are three main types of cannabinoids: herbal cannabinoids that occur uniquely in the cannabis plant, synthetic cannabinoids that are manufactured and endogenous cannabinoids that are produced in vivo. Herbal cannabinoids are nearly insoluble in water but soluble in lipids, alcohol and non-polar organic solvents. These natural cannabinoids are concentrated in a viscous resin that is produced in glandular structures known as trichomes. In addition to cannabinoids, the resin is rich in terpenes, which are largely responsible for the odor of the cannabis plant.

Although cannabidiol (CBD) is the most abundant non-psychotropic plant cannabinoid, it has received considerably less attention than Δ9-tetrahydrocannabinol (THC). Unfortunately, due to the psychotropic effects of THC, use of cannabis has limited medicinal value. THC is well known for not only its psychoactivity but also for its immunomodulatory properties. The identification of THC as a major psychoactive drug and its chemical synthesis in 1964 opened a new era of synthetic cannabinoids as pharmacological agents. Cannabinoid research has increased tremendously during the last 10 years since the discovery of cannabinoid receptors and the endogenous ligands for these receptors. The receptors include CB1, predominantly expressed in the brain, and CB2, primarily found on the cells of the immune system. Cannabinoid receptors belong to a superfamily of G-protein-coupled receptors. They are single polypeptides with seven transmembrane α-helices, and have an extracellular, glycosylated N-terminus and intracellular C-terminus. Both CB1 and CB2 cannabinoid receptors are linked to G1/0-proteins. In addition to these receptors, endogenous ligands for these receptors capable of mimicking the pharmacological actions of THC have also been discovered. Such ligands were designated endocannabinoids and included anandamide and 2-arachidonoyl glycerol (2-AG) (7). Anandamide is produced in the brain and peripheral immune tissues such as the spleen.

Cannabinoids were shown to impair macrophage functions, cause an imbalance in T-cell CD4/CD8 ratio and decrease immunoglobulin production. Cannabinoids also downregulate natural killer (NK) cell and cytotoxic T lymphocyte (CTL) activity.

Unlike THC, which exerts its action by binding to the cannabinoid receptors, CB1 and CB2, CBD does not bind to CB1 receptors and hence has no psychotropic activity. There is some literature on the in vitro and in vivo therapeutic effects of CBD. In addition to its immunomodulating and anti-inflammatory properties, CBD has been reported to exhibit anticonvulsive, anti-anxiety, and antipsychotic activity, and function as an efficient neuroprotective antioxidant. The in vitro suppressive effect of CBD on down-modulating the release of tumor necrosis factor α (TNFα), interleukin 1 (IL-1), and interferon γ (IFN)-γ from peripheral blood cells has also been reported. CBD has demonstrated activity in ameliorating collagen-induced arthritis in mice and has been shown to suppress T-cell responses and the production of TNFα and IFNγ. CBD also inhibits uptake of THC and anandamide and its hydrolysis. Taken together such studies demonstrate that cannabinoids can decrease the immune response as discussed in several reviews. This has led to the intriguing possibility that nonpsychotropic components of *Cannabis* may offer potential as an immunosuppressant.

Despite extensive evidence which suggests that cannabinoids suppress the immune functions, the precise mechanisms involved have not been identified. Several studies have indicated that the observed impairment of macrophage/T-cell cooperation is accompanied by dysregulation in cytokine production by immune cells. The fact that both CB1 and CB2 receptors have been found on the immune cells suggests that cannabinoids play an important role in the regulation of the immune system. Recent studies demonstrated for the first time that THC or CBD when administered into C57BL/6 mice triggers marked apoptosis in lymphocytes and macrophages resulting in atrophy of the thymus and spleen. Together, such studies have raised the exciting possibility that the immunosuppression induced by cannabinoids may result from induction of apoptosis in immune cells.

Preliminary studies have suggested that CBD may act through unique receptors that belong to the transient receptor potential channel vanilloid (TRPV) subfamily in induction of apoptosis. In mammals, this family of thermosensitive receptors found in neurons includes six members, TRPV1, TRPV2, TRPV3, TRPV4, TRPM8, and TRPA1. In addition to the sensory neurons, selected TRPV members such as TRPV1 or also known as capsaicin receptor or vanilloid receptor 1 (VR1) have been reported to be expressed on mast cells, dendritic cells, rat peripheral blood mononuclear cells (PBMC) and thymocyte subsets.

Thus, the role of VR1 in CBD induced apoptosis of T cells is examined. Studies have demonstrated that THC may induce apoptosis through CB1 and CB2. The affinity of CBD for CB2 receptors ($K_i$=96.3+/−14 nM) was found by other investigators to be in approximately the same range as that of THC ($K_i$=36.4+/−10 nM). It has been noted that the effect of CBD on a transformed T cell line was found to be mediated by CB2. Therefore examination of the role of cannabinoid receptors in mediating T cell apoptosis and immunoregulation has been performed. Thus, in accordance with the present disclosure, a method to treat inflammatory diseases such as hepatitis with CBD, independent of cyclo-oxygenase (COX) inhibition, has been performed.

Treatment of Hepatitis

In accordance with one embodiment of the present disclosure, CBD can be administered to a patient suffering hepatitis for treatment thereof. In one particular embodiment, CBD can be administered to the patient without a psychotropic effect, since the CBD can be administered as the natural material isolated from other natural cannabinoids, or as a synthetic purified substance, i.e., substantially or completely free of any psychotropic agents (e.g., THC). It should be understood that, when referring to a treatment that is substantially free of psychotropic agents, minuscule amounts of the psychotropic agents may be present therein. However, such negligible amounts do not create a psychotropic effect on most patients.

The dosage of the cannabidiol to the patient can depend on the disease state or particular condition of the patient, as well as other clinical factors (e.g., weight and condition of the human or animal and the route of administration of the cannabidiol). The cannabidiol can be administered between several times per day to a single treatment protocol. Optionally, the cannabidiol can be delivered according to the disclosed processes either acutely, during a one-time intervention, or chronically, for instance using multiple administrations or optionally a single administration of a timed or sustained releases system. For example, the cannabidiol can be administered to the patient via a drug delivery vehicle, such as a sustained release drug delivery vehicle. It is to be understood that the present disclosure has application for both human and veterinary use. The methods of the present invention contemplate single as well as multiple administrations, given either simultaneously or over an extended period of time. In addition, the cannabidiol can be administered in conjunction with other forms of therapy.

In one embodiment, the cannabidiol can be provided in pharmaceutically acceptable formulations using formulation methods known to those of ordinary skill in the art. These formulations can generally be administered by standard routes, such as via direct injection of the formulation into the patient or orally administered (e.g., in a pill or capsule form).

Compositions of the present invention can include additional agents, in addition to the cannabidiol. Such agents can be active agents, providing direct benefit to the patient in addition to the treatment of hepatitis provided by the cannabidiol, or may be supporting agents, improving delivery, compatibility, or reactivity of other agents in the composition.

Compositions for parenteral delivery, e.g., via injection, of cannabidiol can include pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. In addition, the composition can contain minor amounts of auxiliary substances such as wetting or emulsifying agents, pH buffering agents and the like that can enhance the effectiveness of the cannabidiol. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents.

Prevention of the action of microorganisms may be ensured by the inclusion of various antibacterial and antifungal agents such as paraben, chlorobutanol, phenol, sorbic acid and the like. It may also be desirable to include isotonic agents such as sugars, sodium chloride and the like.

In one embodiment, the compositions can include pharmaceutically acceptable salts of the components therein, e.g., those that may be derived from inorganic or organic acids. Pharmaceutically acceptable salts are well known in the art. For example, S. M. Berge, et al. describes pharmaceutically acceptable salts in detail in J. Pharmaceutical Sciences (1977) 66:1 et seq., which is incorporated herein by reference. Pharmaceutically acceptable salts include the acid addition salts that are formed with inorganic acids such as, for example, hydrochloric or phosphoric acids, or such organic acids as acetic, tartaric, mandelic and the like. Salts formed with free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. The salts may be prepared in situ during the final isolation and purification of the cannabidiol or separately via reaction of a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptonoate, hexanoate, fumarate, hydrochloride, hydrobromide, hydroiodide, 2-hydroxymethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl, and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

In one embodiment, the method can include use of timed release or sustained release delivery systems as are generally known in the art. Such systems can be desirable, for instance, in situations where long term delivery of the cannabidiol to the patient is desired. According to this particular embodiment, a sustained-release matrix can include a matrix made of materials, usually polymers, which are degradable by enzymatic or acid/base hydrolysis or by dissolution. Once located within the patient, such a matrix can be acted upon by enzymes and body fluids. The sustained-release matrix can be chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Possible biodegradable polymers and their use are described, for example, in detail in Brem et al. (1991, J. Neurosurg. 74:441-6), which is hereby incorporated by reference in its entirety.

When an effective amount of the cannabidiol is administered by intravenous or subcutaneous injection, the compositions can generally be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection can contain, in addition to the phenolic compound of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The treatment composition of the present invention may also contain stabilizers, preservatives, antioxidants, or other additives known to those of skill in the art.

EXAMPLES

Preliminary studies have shown that exposure to THC or CBD in mice induces apoptosis in thymocytes and peripheral T cells but not in bone marrow hematopoietic progenitors. These properties make the cannabinoids candidates for therapeutic modality against autoimmune diseases such as hepatitis. While THC, due to psychotropic effects, is not suitable for clinical use, CBD, being non-psychoactive, can constitute an excellent choice for clinical use.

CBD Induces Apoptosis in Thymocytes and Splenocytes

Previous studies have shown that cannabinoids such as $\Delta^9$-tetrahydrocannabinol (THC), an important psychoactive component of the *Cannabis* plant, can trigger apoptosis in immune cells and exhibit anti-inflammatory properties. However, because THC is psychoactive, it is not an appropriate candidate for clinical use. More recently, studies have focused on cannabidiol (CBD) which is yet another constituent of the *Cannabis* plant that is nonpsychoactive and thus has the potential for clinical applications.

Figure 1:
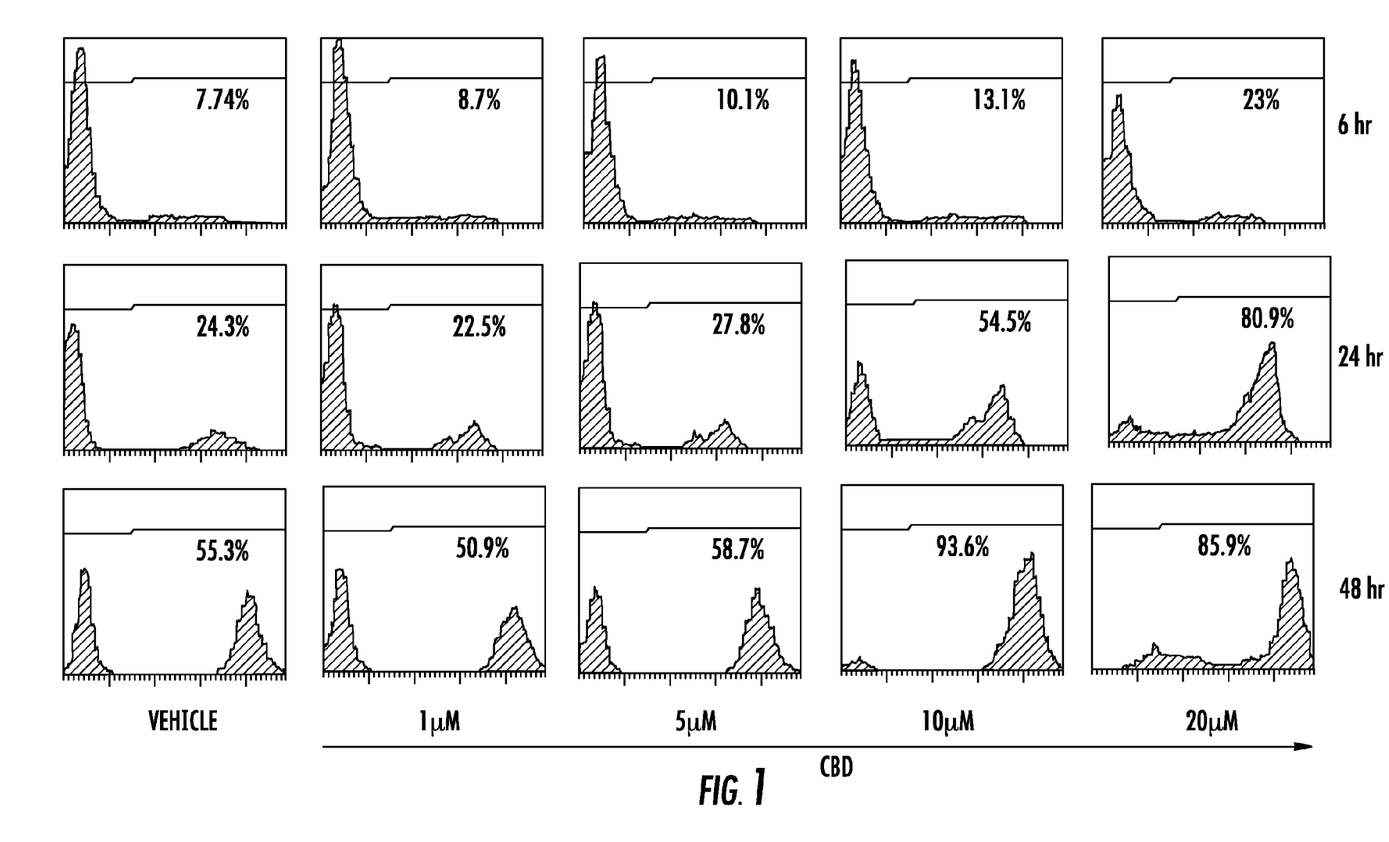
FIG. 1 shows apoptosis induction by CBD in thymocytes. Thymocytes from C57BL/6 mice were cultured with CBD or vehicle and analyzed for apoptosis by TUNEL. Percentage of apoptotic cells is shown in each histogram.

The in vitro efficacy of CBD to induce apoptosis in thymocytes was tested. Thymocytes were harvested from normal C57BL/6 mice and cultured for 6-48 hrs with 1-20 μM CBD dissolved in ethanol as the vehicle and the cells were analyzed for apoptosis using TUNEL assay. As shown in FIG. 1, CBD caused a dose dependent increase in apoptosis at concentrations of about 5 μM or greater. However, at about 1 μM the percent apoptosis was similar to that seen in vehicle-treated cultures as control. It should be noted that thymocytes when cultured in vitro for 24-48 hr do undergo spontaneous apoptosis partially which was evident from data in vehicle-treated groups.

Figure 2:
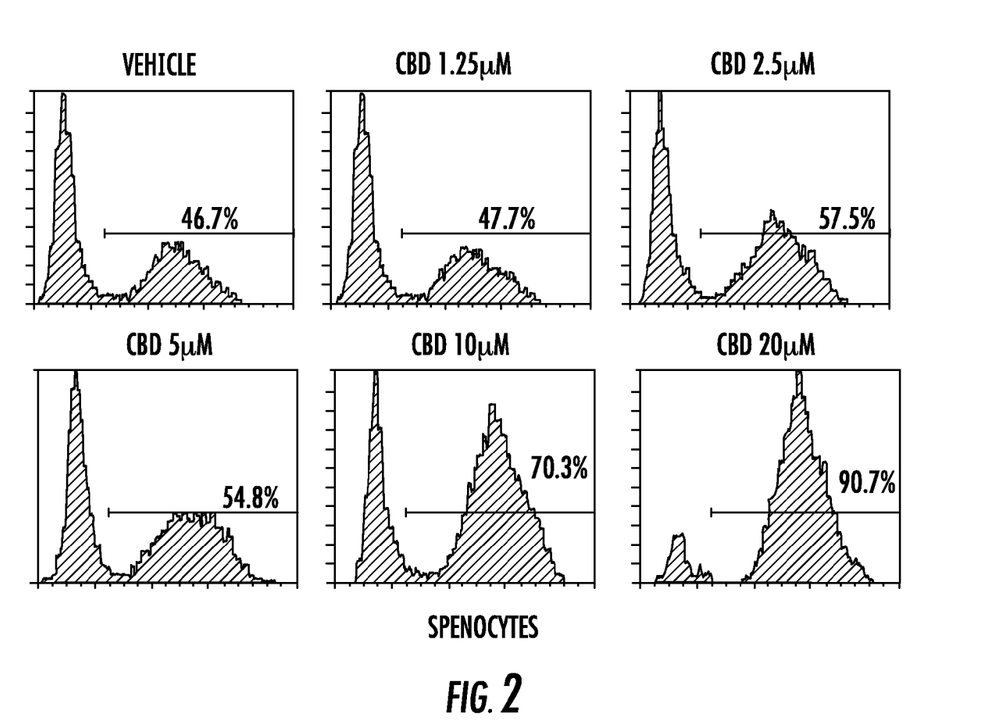
FIG. 2 shows the analysis for apoptosis using TUNEL after 24 hours for splenocytes cultured with vehicle or various concentrations of CBD.

Next, the effect of CBD on apoptosis induction in splenocytes was investigated. Splenocytes from C57BL/6 mice were cultured with various concentrations of CBD for 24 hrs and apoptosis was analyzed by TUNEL. As seen from FIG. 2, CBD caused a dose dependent increase in apoptosis of splenocytes. Concentrations of about 2.5 μM and above can induce apoptosis.

Figure 3:
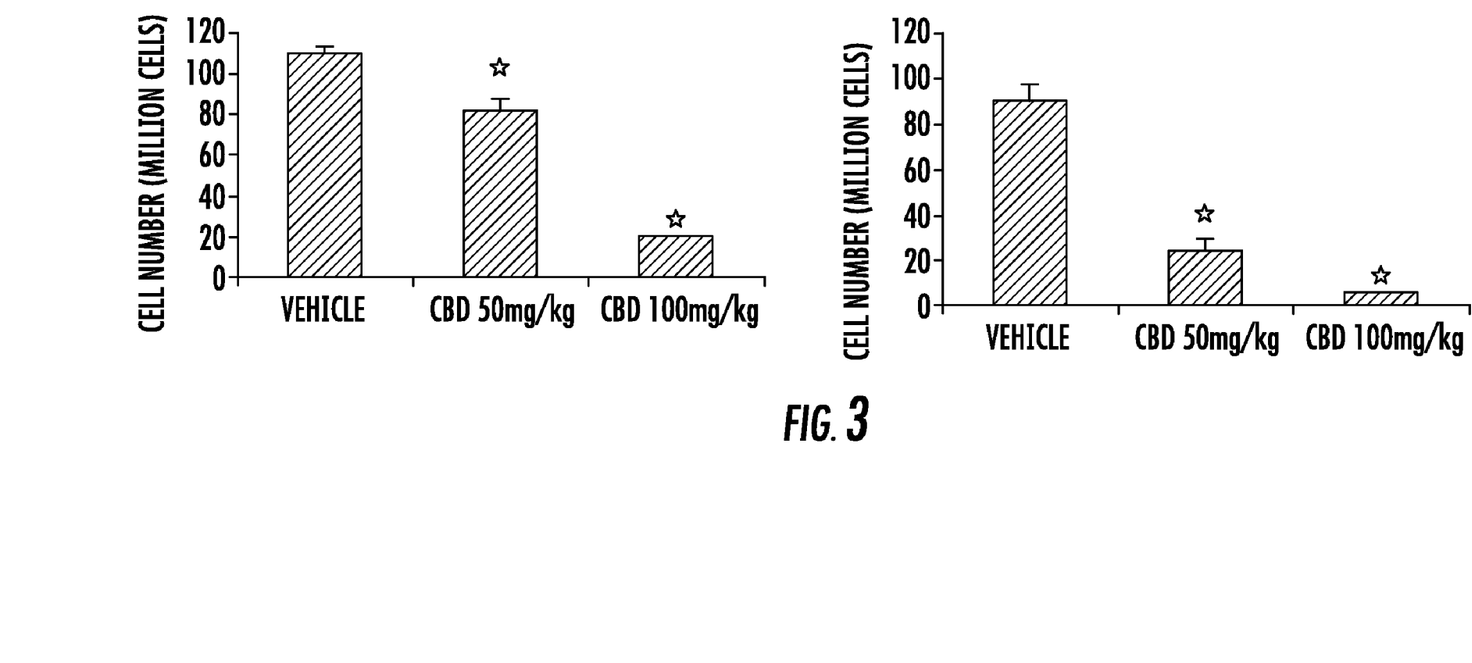
FIG. 3 shows that CBD treatment in vivo leads to decreased cellularity in the thymus (left panel) and spleen (right panel). Groups of 5 C57BL/6 mice were injected with vehicle or CBD and 24 hr later, total viable cellularity was determined. The data show mean cellularity/organ ±S.E. * denotes p<0.01.

Treatment of Mice with CBD Causes Significant Depletion of Cells in the Thymus and Spleens Next it was determined whether administration of CBD into mice would trigger apoptosis and loss of cells. Groups of 5 mice were treated with vehicle or CBD preparation at 50 or 100 mg/kg body weight. After 24 hr, the thymi and spleens were harvested and the cells were enumerated for viability using trypan blue dye exclusion. The data shown in FIG. 3 indicates that CBD treatment caused a dose dependent decrease in thymic and splenic cellularity.

CBD Inhibits the Proliferative Responsiveness of T and B Cells

Figure 4:
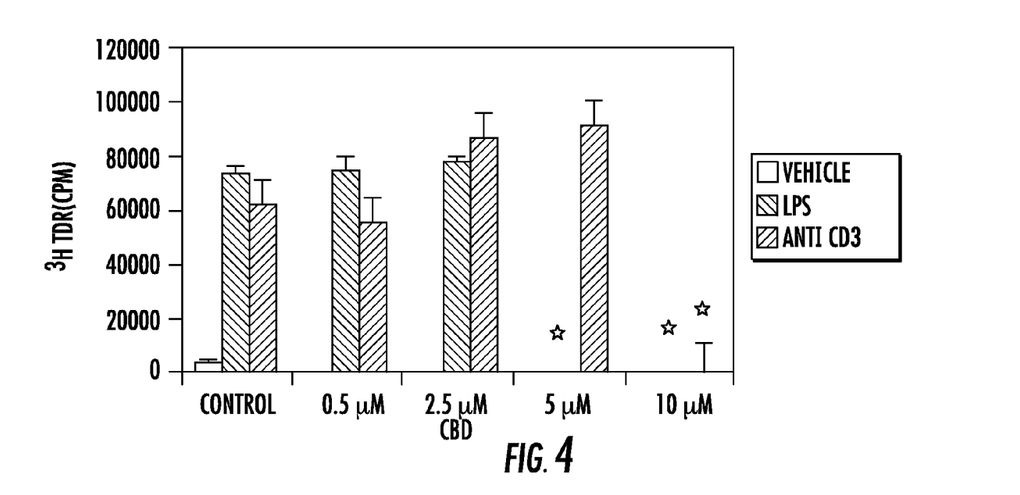
FIG. 4 shows the effect of CBD on proliferation of T and B lymphocytes. Normal splenocytes were cultured with LPS or anti-CD3 mAbs for 48 hr and cell proliferation was measured by thymidine incorporation assay. Vertical bars represent means of triplicate cultures ±SEM. * denotes p<0.01.

To investigate if CBD would affect the proliferative responsiveness of T and B cells, splenocytes were cultured with various concentrations of CBD or the vehicle either alone or with LPS or anti-CD3 mAbs to activate selectively B and T cells respectively. Forty eight hours later, cell proliferation was measured by thymidine incorporation assay. The data shown in FIG. 4 indicates that activated B cells are more sensitive than activated T cells inasmuch as about 5 μM CBD completely decreased the response, while at this concentration, T cell proliferation was not affected. However, at about 10 μM CBD, the T cell proliferative response was also completely inhibited along with that of B cells.

Figure 5:
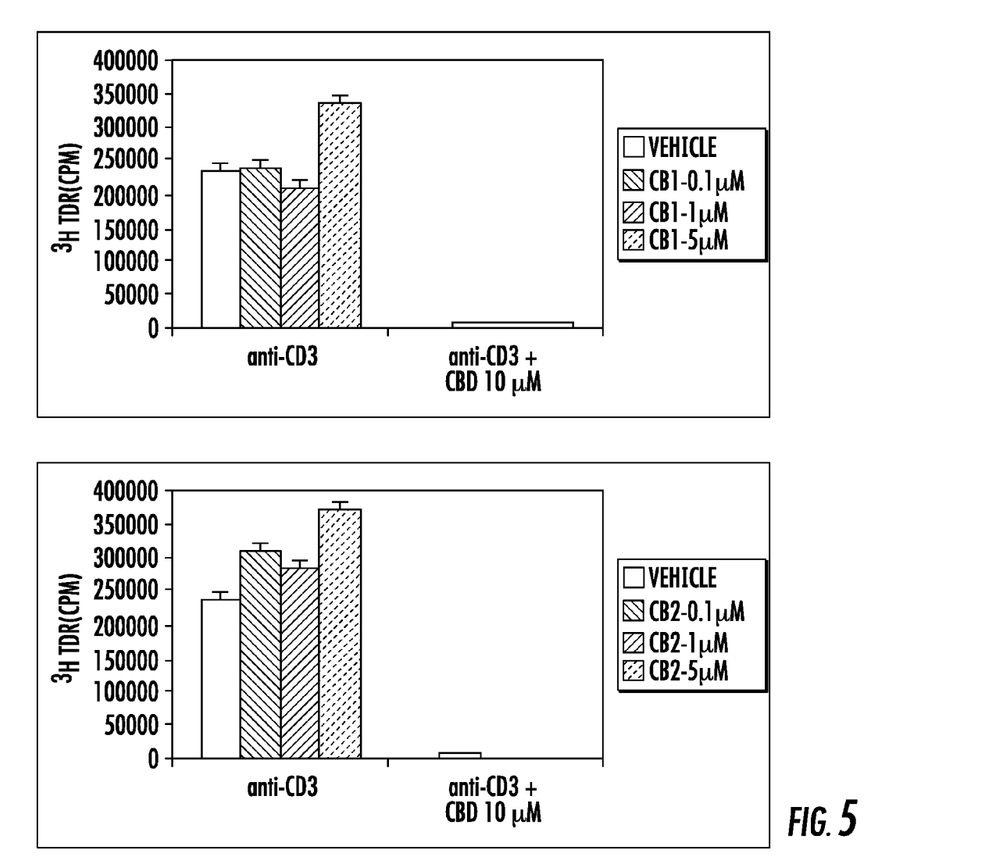
FIG. 5 shows the role of CB1 and CB2 receptors in CBD-induced decrease in T cell proliferation. Splenocytes were cultured with anti-CD3 mAbs as described in FIG. 4, in the presence or absence of various concentrations of CB1 and CB2 antagonists. Cell proliferation was measured by thymidine incorporation assay.

Role of CB1 and CB2 Cannabinoid Receptors on CBD Induced Decrease in Cell Proliferation CBD has been shown to have little or no activity against cannabinoid receptor CB1, which is expressed in the central nervous system (CNS) and to some extent on immune cells, and moderate activity against CB2 that is exclusively expressed in immune cells. Splenocytes were cultured with anti-CD3 mAbs to activate T cells in the presence of vehicle or various concentrations of CB1 or CB2 receptor antagonists, SR141716A and SR144528, respectively. The CB1 and CB2 receptor antagonists failed to block the CBD-induced decrease in T cell proliferative response (FIG. 5). These data demonstrate that CBD-induced suppression of cell proliferation was independent of CB1 and CB2 receptors. It should be noted that in this experiment, the CB1 and CB2 receptor antagonists when used in the absence of CBD, failed to exhibit a significant effect. Moreover, it has been previously shown that these concentrations of CB1 and CB2 receptor antagonists can block the effects of THC.

Role of Caspases and CB1 and CB2 Receptors in THC- and CBD-Mediated Apoptosis

Figure 6:
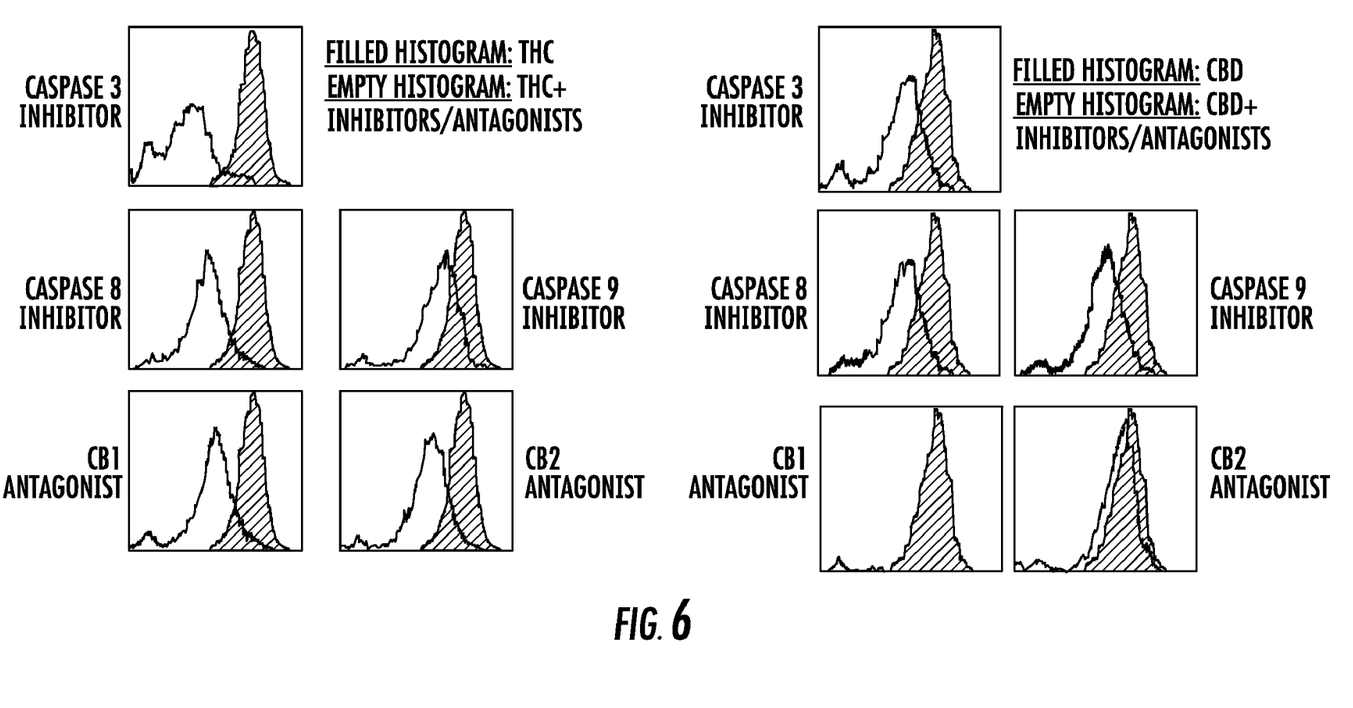
FIG. 6 shows the effect of caspase inhibitors and CB1 and CB2 antagonists on THC- and CBD-induced apoptosis. Thymocytes were cultured with 10 µM THC or CBD for 24 hr in the presence of various inhibitors or antagonists. The cells were analyzed for apoptosis using TUNEL. The caspase inhibitors or antagonists of cannabinoid receptors when used alone fail to induce apoptosis when compared to vehicle controls (data not shown).

Next, the caspase-dependence of CBD-induced apoptosis in thymocytes was investigated, using inhibitors as described. The mediation of apoptosis induction through cannabinoid receptors, CB1 and CB2, was also investigated. To this end, splenocytes were cultured with about 10 μM THC or CBD for 24 hr in the presence of various inhibitors or agonists or the appropriate vehicle. The data shown in FIG. 6 demonstrates that THC-induced apoptosis in thymocytes was significantly blocked by caspase 3 inhibitor as well as inhibitors of caspase 8 and 9, thereby demonstrating that THC-induced apoptosis involved caspases and that both the death receptor pathway and the mitochondrial pathway were involved. Furthermore, CB1 and CB2 antagonists could significantly block THC-induced apoptosis. Interestingly, when these experiments using CBD were repeated, the involvement of caspases was noted. However, CB1 antagonist completely failed to block apoptosis while CB2 antagonist blocked it partially. These data demonstrate that THC-induced apoptosis was caspase-dependent involving both the intrinsic and extrinsic pathways of apoptosis. These data also demonstrate that CBD-induced apoptosis was caspase-dependent involving both the intrinsic and extrinsic pathways of apoptosis. These data also demonstrate that CBD-induced apoptosis was CB1 receptor independent and that CB2 receptors might play a minor role.

Role of Vanilloid Receptor (VR1) on CBD Induced Apoptosis

Figure 7:
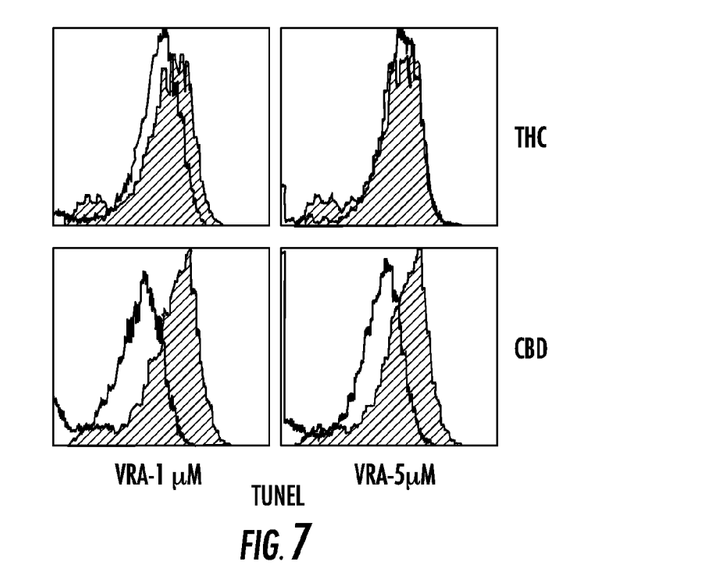
FIG. 7 shows the role of vanilloid receptors in CBD-induced apoptosis. Thymocytes were cultured with 10 µM of THC or CBD for 48 hours in the presence of vanilloid receptor antagonists. The filled histograms show cells cultured with THC or CBD and the empty histograms show cultures incubated with THC/CBD+VR antagonist (VRA). The antagonists by themselves did not have any significant effect on apoptosis (data not shown).

In addition, the possibility that CBD was acting through vanilloid receptors was investigated. Vanilloid receptors are expressed mainly by primary sensory neurons involved in nociception and neurogenic inflammation. Capsaicin, the pungent compound of red pepper, mediates its effect primarily through vanilloid receptors that can act as voltage-independent channels. Recent studies have shown that Vanilloid receptor 1 (VR1) is not only expressed on primary neurons of the CNS but also on immune cells, including thymocytes. Furthermore, VR1 has been shown to be involved in apoptosis. Notably, CBD has recently been shown to act as a VR-1 agonist of potency equivalent to capsaicin. To this end, the thymocytes with THC or CBD as described in the previous figure were cultured in the presence or absence of vanilloid receptor antagonist, capsazepine. As shown in FIG. 7, THC-induced apoptosis was not altered by VR1 antagonist. Interestingly, however, CBD-induced apoptosis was significantly inhibited by VR1 antagonist. These data demonstrate the exciting possibility that CBD mediates apoptosis in normal T cells through vanilloid receptors.

Role of CB2 in CBD-Induced Apoptosis in Transformed Jurkat T Cells

Figure 8A:
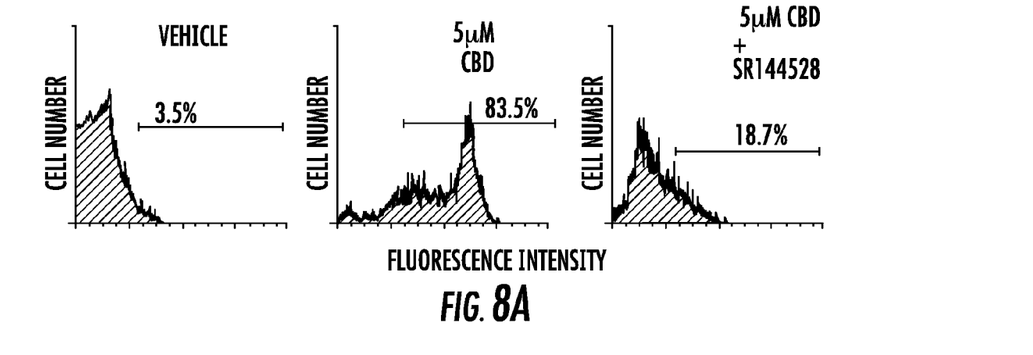
FIG. 8 shows the role of CB2 in mediating CBD-induced apoptosis in Jurkat cells. The role of CB2 in mediating CBD-induced apoptosis was determined by culturing Jurkat tumor cells for 16 hours with 5 µM CBD in the presence or absence of CB2 antagonist (SR144528). Apoptosis was assayed using the (A) TUNEL and (B) Wright-Giemsa staining methods.
Figure 8B:
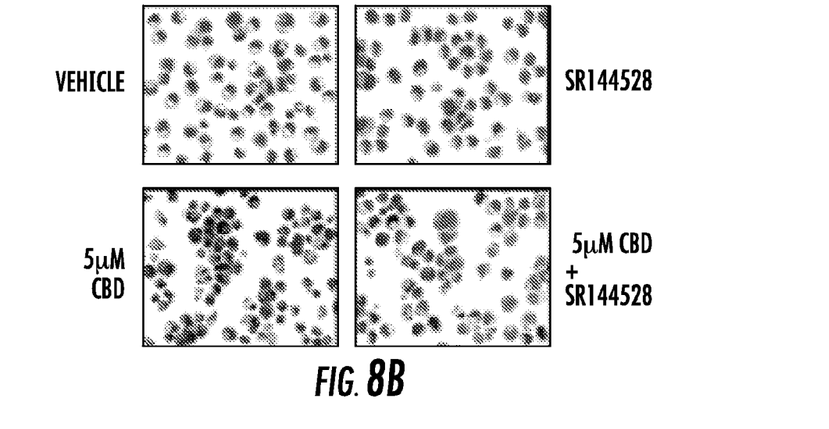

It has been shown that normal and transformed T cells may differ in their sensitivity and signaling pathways of apoptosis. It has also been shown that CBD can induce apoptosis in a wide range of transformed T cells, including Jurkat cells. Therefore it was examined whether CBD was acting through CB1 or CB2 receptors to induce apoptosis. To this end, Jurkat cells were incubated with about 5 µM CBD (or the vehicle as control) in the presence of CB1- or CB2-selective antagonists. After 16 h, CBD-induced apoptosis by TUNEL was examined (FIG. 8A) and Wright-Giemsa staining (FIG. 8B) methods. The results from the TUNEL assay showed that exposure of Jurkat cells to about 5.0 µM CBD led to the induction of apoptosis in 83.5% of the cells compared to 3.5% observed in the vehicle treated cells. However, if the Jurkat cells were pre-exposed to the CB2-selective antagonist, SR144528, the level of CBD-induced apoptosis was significantly reduced to 18.7%. Similar results were seen using the Wright-Giemsa assay, where it was shown that following exposure to about 5.0 µM CBD the majority of the Jurkat cells displayed classical morphological features of apoptosis, including nuclear condensation, cell shrinkage, and formation of apoptotic bodies. In contrast, Jurkat cells pretreated with SR144528 displayed significantly fewer signs of apoptosis following CBD exposure. Treatment with either the CB1 antagonist was unable to prevent cannabidiol-induced apoptosis. Together, these results demonstrate that cannabidiol-induced apoptosis of Jurkat cells was mediated, at least in part, through CB2.

Cannabidiol Induces Activation of the Caspase Cascade Through CB2

Figure 9:
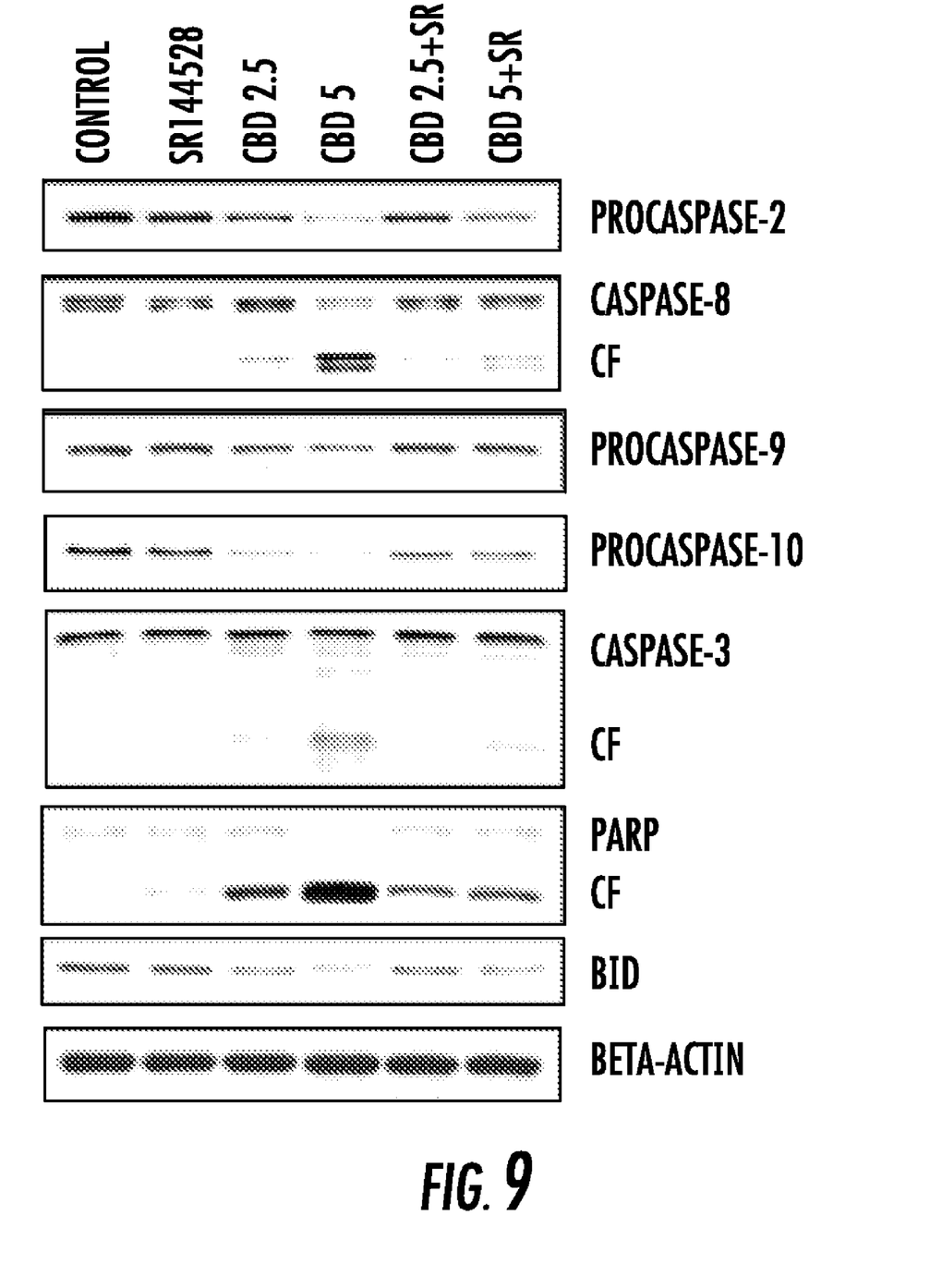
FIG. 9 shows that cannabidiol induced activation of the caspase cascade through activation of CB2. Jurkat T cells were exposed to various concentrations of CBD (2.5 or 5.0 µM) of the vehicle for 16 hours. The role of CB2 in the activation of caspases was monitored by culturing Jurkat cells with CBD (2.5 or 5.0 µM) as well as the CB2-selective antagonist, SR144528. Next, the cells were lysed, the cellular proteins were isolated and Western analysis was performed. The levels of the procaspases as well as the presence of the cleaved form (CF) of various caspases were examined.

To further investigate the mechanism of cannabidiol-induced apoptosis, the activation pattern of caspases following CBD exposure was examined. To this end, Jurkat cells were exposed to various concentrations of cannabidiol (about 2.5, and about 5 µM) or the vehicle for 24 hours, after which, the cells were harvested and the presence of the various caspases was determined by Western blot analysis. The results (FIG. 9) demonstrate that exposure to CBD at concentrations of about 2.5 µM or greater lead to activation of the caspase cascade. More specifically, cleavage of caspase-8, and reduction in procaspase-2, 9, and 10, which are thought to be involved in initiating the caspase cascade were observed. In addition, the cleavage of the effector type caspase-3 and PARP were observed following exposure to CBD. Next, the involvement of CB2 was examined by culturing Jurkat cells with the CB2 antagonist, SR144528, in the presence or absence of CBD. The results showed that the CB2 antagonist was able to significantly prevent CBD-mediated induction of the caspase cascade. Interestingly, CBD-induced cleavage of Bad was observed in Jurkat cells suggesting possible cross-talk between the intrinsic and extrinsic apoptotic pathways. Together, the studies using transformed T cells suggest that CB2 receptors clearly play a critical role in CBD-mediated apoptosis. Thus, further investigations will be done on the role of CB2 and VR-1 receptors in apoptosis induction in vivo against naïve and activated T cells.

Figure 10:
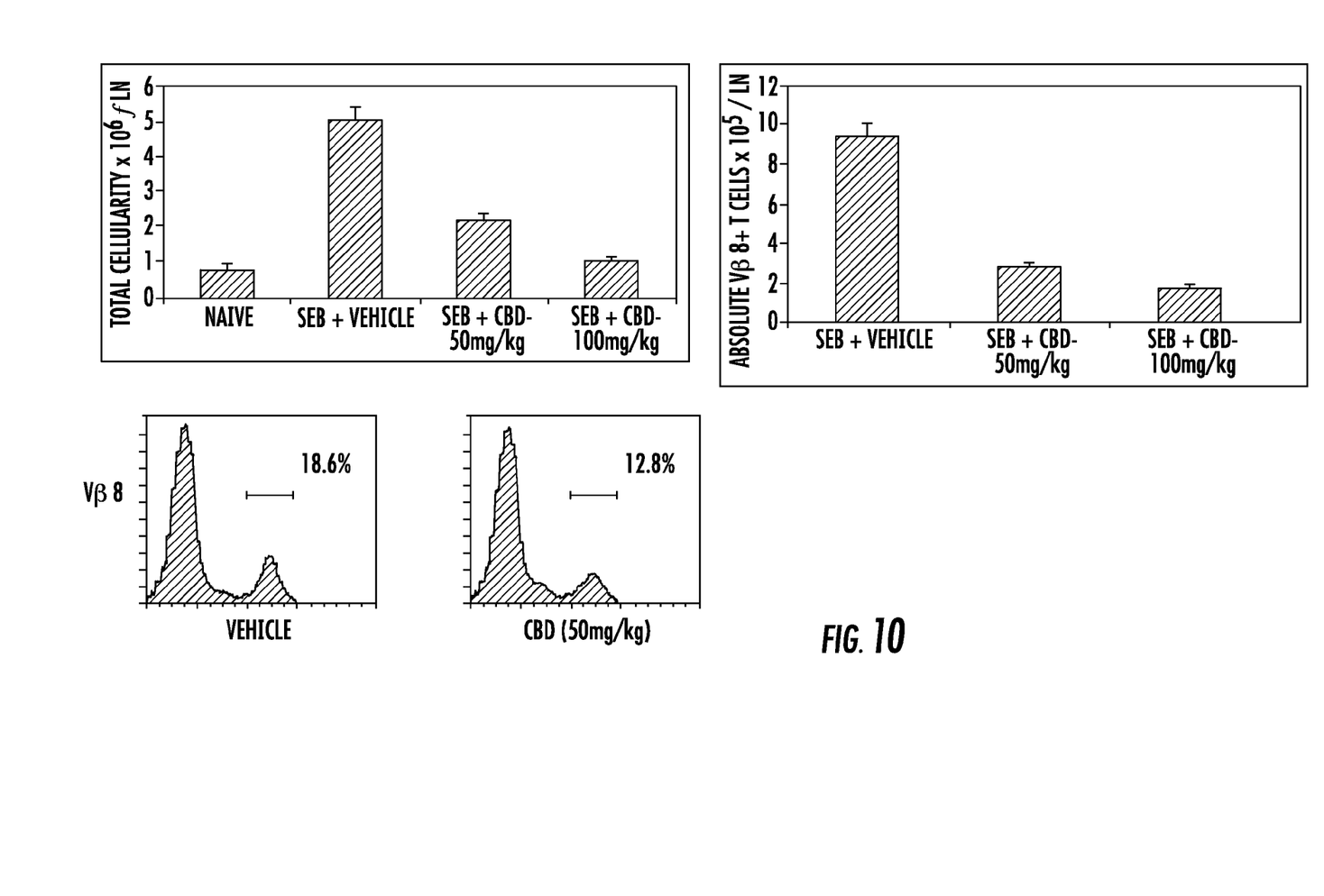
FIG. 10 shows the effect of CBD and SEB-induced activation of T cells. Groups of 5 C57BL/6 mice were injected SEB (10 µg) in the footpad on day 1, followed by CBD by i.p route the same day (day 1) and on days 2 and 3. On day 4, the popliteal lymph nodes (LN)s were removed and total viable cellularity was determined. The data were expressed as mean+/−SEM cellularity/LN. Panel C shows staining for Vβ8 in mice.

Effect of CBD on Staphylococcal Enterotoxin B (SEB)-Induced Activation of T Cells SEB is a superantigen and extremely potent activator of T cells by virtue of the fact that it can activate a large number of T cells that express certain Vβ specific TCR including Vβ8. Because of its ability to induce a strong immune response, and to trigger autoimmune hepatitis, we used this model to address whether CBD administration in vivo would suppress the immune response against SEB. SEB was injected into the footpads of C57BL/6 mice and they were treated with CBD at about 50 mg or about 100 mg/kg body weight. On day 4, the popliteal lymph nodes were harvested and total cellularity/lymph node was calculated. In addition, the lymph nodes were stained with Abs against Vβ8. The data shown in FIG. 10 indicates that naïve animals have approximately 1 million cells/popliteal lymph node. Following SEB immunization, there was almost a five-fold increase in lymph node cellularity. Interestingly, CBD caused a dose dependent decrease in lymph node cellularity thereby demonstrating that CBD was able to decrease the SEB specific T cell proliferation. When the lymph nodes were stained and analyzed for Vβ8+cells as shown in FIG. 10, vehicle treated SEB immunized mice showed 18.6% Vβ8+ T cells which dropped to 12.8% following injection of CBD at 50 mg/kg body weight. Furthermore, when the absolute Vβ8+ T cell numbers were calculated CBD was found to induce a dose dependent decrease in SEB reactive Vβ8+ T cells. Together, these data demonstrate that CBD is very effective at down regulating the robust immune response generated by SEB.

Figure 11:
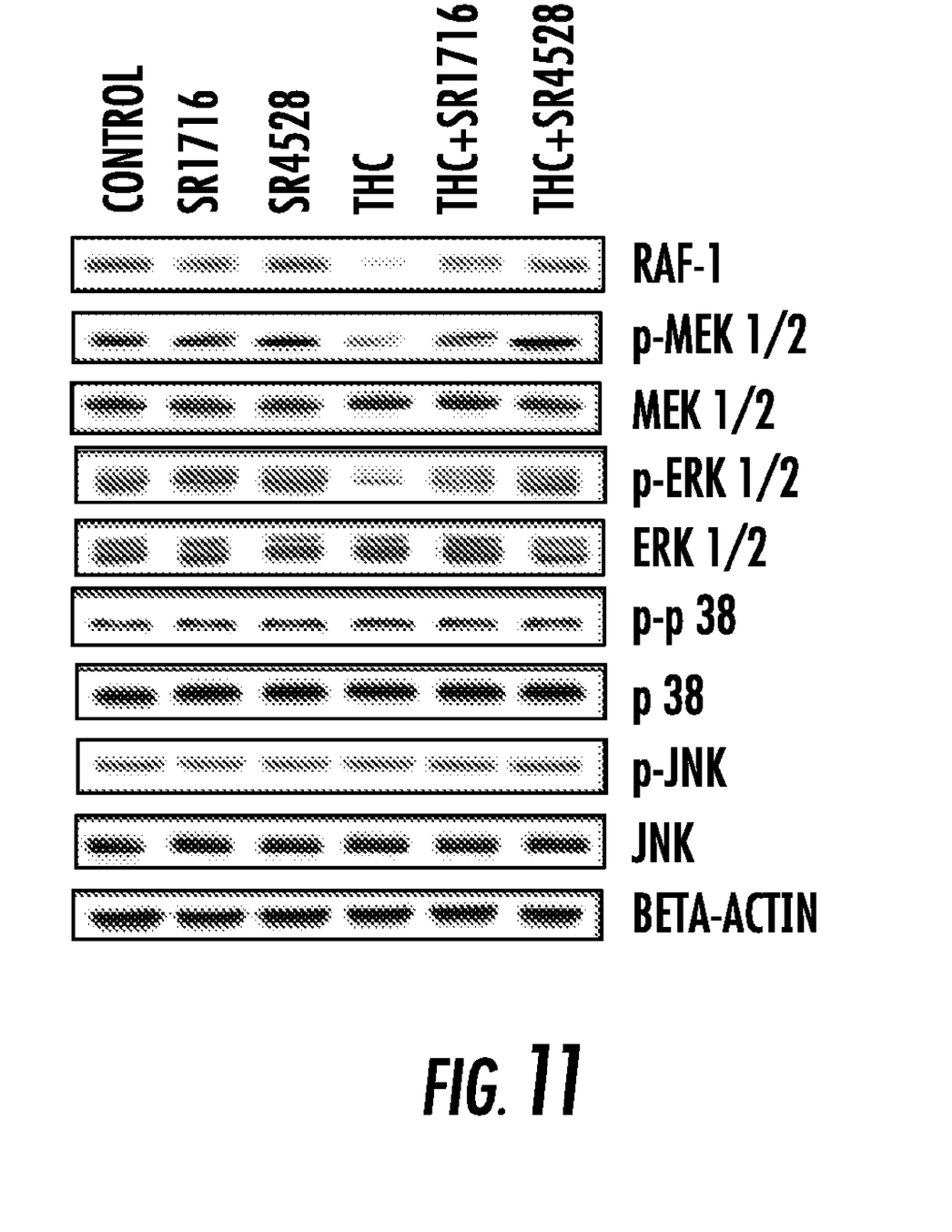
FIG. 11 shows the Western blot analysis used to monitor the expression of Raf-1, phosphor-MEK1, total MEK, phosphor-ERK, total ERK, phosphor-p38 MAPK, total p38 MAPK, phosphor-JNK, and total JNK for Jurkat cells treated with 10 µM THC or the vehicle for a total of 12 hours.

Suppression of Raf-1/MEK/ERK Cytoprotective Signaling Pathway Induced by Cannabinoids Extensive studies have been performed to identify the signaling pathways that trigger apoptosis induced by cannabis plant-derived cannabinoids. Some of the studies generated by using THC and a human Jurkat T cell line in which THC induces apoptosis have been depicted. MAP kinases (MAPKs) have been implicated in regulation of apoptosis in response to various stimuli. To investigate the potential involvement of this event in THC-induced apoptosis, coculture of CB antagonists was monitored in Jurkat cells exposed to either about 2 μM SR141716 (CB1 receptor antagonist) or about 4 μM SR144528 (CB2 Receptor antagonist) ±10 μM THC for a total 1 h. Interestingly, whereas exposure of the Jurkat cells to the cannabinoid antagonists alone had little effect on Raf-1 expression (FIG. 11), exposure of the cells to THC alone resulted in a very pronounced reduction in level of this protein. In addition, THC treatment diminished the levels of phosphorylation of MEK, with the total MEK expression remaining unchanged with any treatment. Similarly, phosphorylation of ERK1/2 was largely decreased in THC-treated cells, but total ERK1/2 expression, like that of MEK, remained unperturbed under all conditions. However, none of the THC concentrations tested induced alterations in phospho-p38 or phospho-JNK. Also, no changes were observed in levels of total p38 or JNK.

Figure 12:
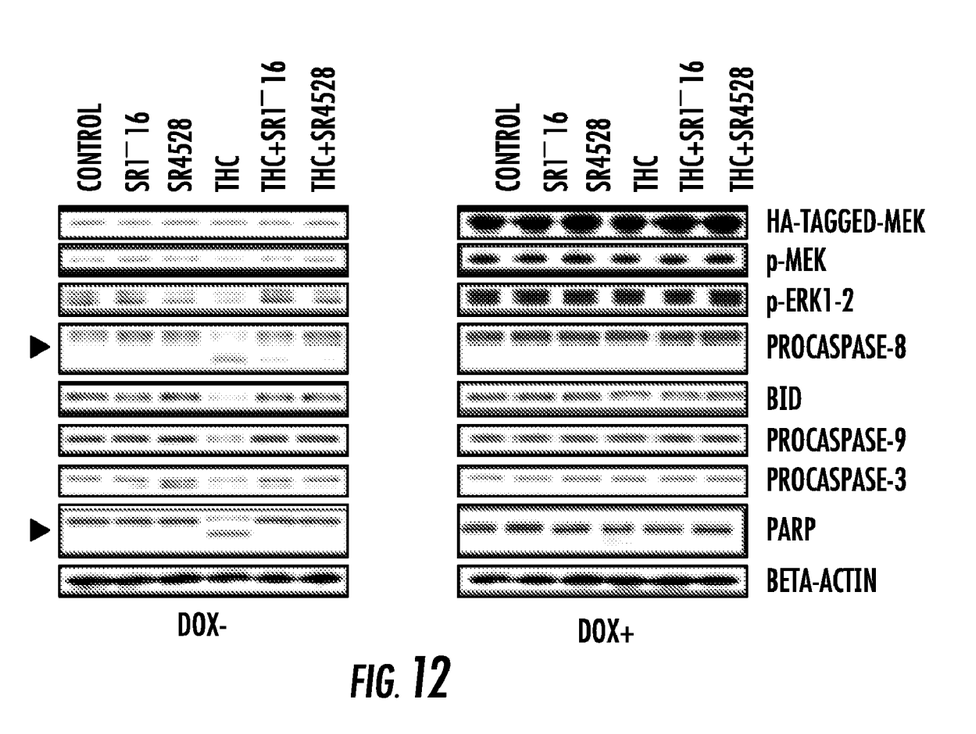
FIG. 12 shows that enforced activation of MEK1/ERK1/2 blocks THC-mediated apoptosis. Jurkat cells inducibly expressing a constitutively active, HA-tagged MEK vector under the control of a tetracycline-responsive promoter were exposed to THC or the vehicle or CB receptor antagonists for a total of 24 hours in the presence or absence of 2 µg/mL doxycycline. Western analysis was used to monitor expression of the HA tag, and various proteins. Arrows represent THC-induced breakdown products or active caspases.

Enforced Activation of MEK1/ERK1/2 Substantially Blocks THC-Mediated Mitochondrial Injury, Caspase Activation, DNA Fragmentation and Apoptosis in Jurkat T Cells Previous studies have indicated that the Raf-1/MEK/ERK1/2 pathway plays a largely cytoprotective role. Based on this, THC-mediated down regulation of the MAPK signaling contributes to the marked potentiation of apoptosis. To define the functional role of enforced activation of MEK/ERK in regulating THC-induced cell death, a Jurkat cell line that inducibly expresses a constitutively active MEK construct (Mek/30) under the control of a doxycyline-responsive promoter was employed. Exposure to THC in the absence of doxycycline resulted in apoptosis in nearly 50% of cells, whereas apoptosis was essentially abrogated in the presence of doxycycline at 12 hours. Western analysis revealed that cells cultured in the absence of doxycycline displayed minimal expression of a HA-tag and modest basal expression of phospho-MEK (FIG. 12). However, when cells were cultured in the presence of doxycycline, a pronounced increase in expression of the HA tag was noted, along with substantial increases in expression of both phospho-MEK and -ERK. Enforced activation of ERK1/2 also diminished THC-mediated activation of procaspase-8, bid, -9 and -3, as well as PARP degradation.

Figure 13:
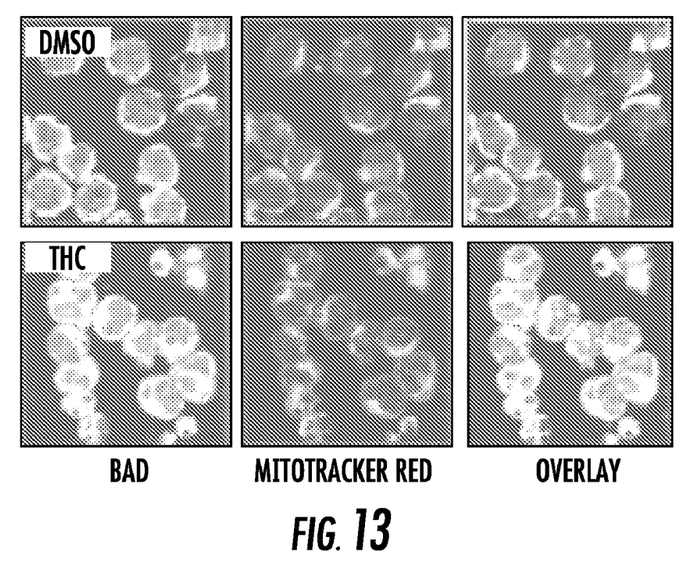
FIG. 13 shows mitochondrial localization of Bad in THC-stimulated cells. Jurkat cells treated with 10 µM THC of the vehicle were harvested and subjected to double-staining with anti-BAD antibodies, followed by a mitochondrion-specific dye (Mitotracker Deep Red 633) and $Cy_2$-labeled secondary Abs, and then analyzed by confocal microscopy.

Analogous to results obtained with the inducible MEK system, in the absence of doxycycline, THC treatment alone resulted in the unequivocal induction of DNA fragmentation. When cells were cultured in the presence of doxycycline, DNA degradation was completely blocked in all treated-conditions. Taken in conjunction with the preceding findings, these observations suggest that interruption of Raf/MEK/ERK pathways by the THC regimen plays an important functional role in THC-induced apoptosis Mitochondrial Localization of Bad in THC-Stimulated Cells Recently, RSK was demonstrated to promote cell survival through phosphorylation and inactivation of the proapoptotic Bcl-2 family member, Bad. Therefore, it was tested whether Bad played a role in THC-induced apoptosis involving Raf/MEK/ERK pathway. Bad resides in the cytosol but translocates to the mitochondria following death signaling. Confocal microscopy was used to study the translocation of Bad, following exposure of Jurkat cells to THC (FIG. 13). Double-immunofluorescence analysis with anti-Bad Abs and mitochondria-specific dye (MitoTracker Deep Red 633) showed a strong association of Bad with mitochondria in THC-treated cells, when compared to vehicle-treated cells. Together, these studies demonstrate that THC down regulates the Raf/MEK/ERK/RSK pathway in Jurkat cells thereby facilitating translocation of Bad to the mitochondria and consequent apoptosis. Currently, similar studies are being performed to identify the molecular pathways of apoptosis induced by CBD which is acting through VR-1 receptors.

Effect of CBD on Con A-Induced Autoimmune Hepatitis (CAH)

Figure 14:
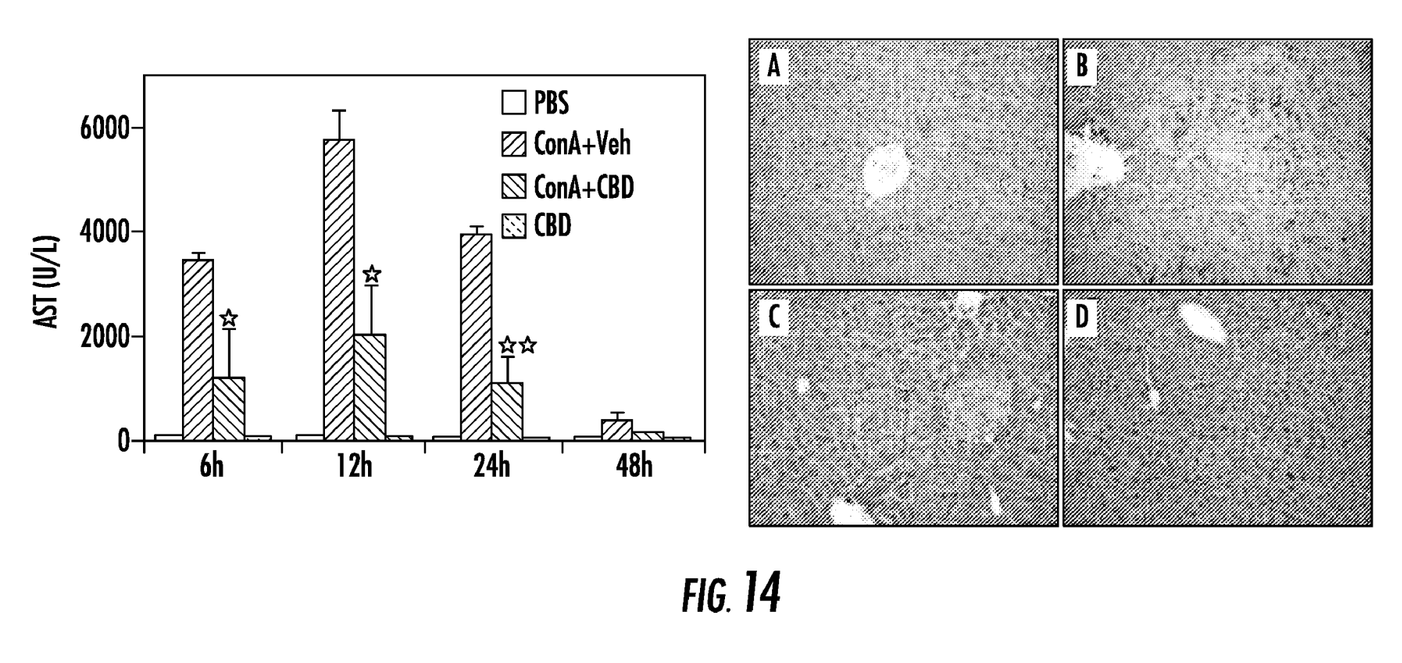

A single injection of concanavalin-A (Con A) has been shown to induce hepatitis in mice and has been shown to represent human autoimmune hepatitis. ConA can directly induce hepatitis and within 8-24 h, clinical and histological evidence of hepatitis occurs, with elevation of transaminase activities in the plasma and hepatic lesions characterized by massive leukocyte accumulation and hepatic necrosis. It was investigated whether CBD can be used in the treatment of CAH. To this end, six C57BL/6 mice were injected with PBS (control), or ConA (12.5 mg/kg bdwt, i.v.) to induce hepatitis. ConA injected mice were administered (i.p.) with ethanol vehicle (ConA+Veh group) or CBD, about 50 mg/kg body wt (ConA+CBD group), on the same day as ConA injection. Some mice received CBD alone (CBD group). Next, blood was collected at 6, 12, 24 and 48 h by retro-orbital bleeding. Plasma AST (aspartate transaminase) was determined by spectrophotometry using AST assay kit, as described. As shown in FIG. 14, Con A injection triggers a significant increase in the plasma AST level, thereby indicating that hepatitis was induced after Con A. Increased AST levels were seen as early as 6 h after Con A injection, reaching a peak at 12 h and declining thereafter. At 48 h, the plasma AST reached normal levels. Interestingly, CBD administration caused marked decrease in AST levels at all time points tested (FIG. 14). Hematoxylin-eosin staining of liver section was conducted 48 h after Con A challenge because of significant liver damage seen at this time point. Damage to hepatocytes and presence of mixed inflammatory infiltrate consisting of lymphocytes, macrophages, and neutrophils was observed in mice injected with Con A alone. However, in ConA+CBD-treated groups, the liver damage was significantly reduced with decreased inflammatory response (FIG. 14), thereby corroborating that CBD was protecting the autoimmune liver injury. In summary, these studies demonstrate that:

1. CBD induces apoptosis in thymocytes and splenocytes in vitro and when injected in vivo, causes decreased cellularity in the thymus and spleen, thereby showing that CBD can act on naïve cells.
2. CBD inhibits the proliferative responsiveness of T and B cells; however, this effect is independent of CB1 and CB2 receptors.
3. CBD-induced apoptosis is caspase-dependent, involving both the intrinsic and extrinsic pathways.
4. CBD-mediated apoptosis in normal T cells is regulated primarily through vanilloid receptors and to a minor degree with CB2. In contrast, CBD-induced apoptosis in transformed T cells is primarily mediated through CB2.
5. CBD suppresses the staphylococcal enterotoxin B (SEB)-induced activation of Vβ8+ T cells in vivo.
6. Cannabinoids such as THC down regulate the Raf/MEK/ERK/RSK pathway in Jurkat T cells thereby facilitating translocation of Bad to the mitochondria and consequent apoptosis.
7. CBD effectively protects the host from autoimmune hepatitis induced by ConA as evidenced by decreased AST levels and marked decrease in inflammatory response.

The foregoing description of the invention and examples along with other modifications and variations to the present invention may be practiced by those of ordinary skill in the art, without departing from the spirit and scope of the present invention. In addition, it should be understood that aspects of the various embodiments may be interchanged both in whole and in part. Furthermore, those of ordinary skill in the art will appreciate that the foregoing description is by way of example only, and is not intended to limit the invention.

What is claimed:

1. A method of treating autoimmune hepatitis in a subject, the method comprising:
   identifying a subject suffering from autoimmune hepatitis; and
   injecting cannabidiol into the subject; wherein said cannabidiol is synthetic cannabidiol or natural cannabidiol isolated from other natural cannabinoids.

2. The method as in claim 1, wherein said cannabidiol is injected to the subject substantially free of any psychotropic agent.

3. The method as in claim 1, wherein said cannabidiol is injected to the subject substantially free of $\Delta^9$-tetrahydrocannabinol.

4. The method as in claim 1 further comprising providing said cannabidiol in a drug delivery vehicle.

5. The method as in claim 4, wherein the drug delivery vehicle is a sustained release drug delivery vehicle.

6. The method as in claim 1, wherein the method is an in vivo therapeutic treatment method.

* * * * *